United States Patent [19]
Delanghe et al.

[11] Patent Number: 5,977,406
[45] Date of Patent: Nov. 2, 1999

[54] PROCESS FOR PREPARING α-AMINO ACID AMIDES, α-AMINO ACIDS AND DERIVATIVES THEREOF

[75] Inventors: Patrick H. M. Delanghe, Maastricht, Belgium; Anna M. C. F. Castelijns, Beek; Paulus L. Alsters, Sittard, both of Netherlands

[73] Assignee: DSM NV, Heerlen, Netherlands

[21] Appl. No.: 08/975,302

[22] Filed: Nov. 20, 1997

[30] Foreign Application Priority Data

Nov. 26, 1996 [BE] Belgium .............................. 09600984

[51] Int. Cl.⁶ ..................... C07C 227/18; C07D 263/20
[52] U.S. Cl. ........................... 562/443; 548/230
[58] Field of Search .............. 548/230; 562/443

[56] References Cited

U.S. PATENT DOCUMENTS

| | | | |
|---|---|---|---|
| 2,571,940 | 10/1951 | Pfister et al. | 548/230 |
| 3,407,226 | 10/1968 | Chemerda et al. | 548/230 |
| 5,153,358 | 10/1992 | Zydowsky | 562/443 |
| 5,298,516 | 3/1994 | Ishihara et al. | |
| 5,356,918 | 10/1994 | Ishihara et al. | |

FOREIGN PATENT DOCUMENTS 0 506 434 A1  9/1992  European Pat. Off. .

OTHER PUBLICATIONS

Iribe et al., '*N–Substituted Phenylpropylamine Derivatives*', Chemical Abstracts, vol. 80, No. 21, p. 399, (May 1994), Abstract No. 120509, JP 49 007 232 A.

'*2–Oxooxazolidine–4–carboxylic Acids*', Chemical Abstracts, vol. 103, No. 1, p. 572 (Jul. 1985), Abstract No. 6331, JP 60 034955 A.

'*2–Oxo–4–cyanooxazolidines*', Chemical Abstracts, vol. 103, No. 1, p. 572 (Jul. 1985), Abstract No. 6332, JP 60 034954 A.

Hennion et al., '*Reactions of .alpha.–ketols Derived from Tertiary Acetylenic Carbinols. III. The Preparation of 4–methyl–4,5,5–trisubstituted–2–oxazolidin Ones*', Journal of Organic Chemistry, Deel 23, pp. 662–664 (1958).

Ashraf et al., '*Synthesis of L–.betha.hydroxy Amino Acids Using Serine Hydroxymethyltransferase*', Tetrahedron, vol. 48, No. 12, pp. 2507–2514 (1992).

Blaser et al., '*Benzyl (R)– and (S)–2–tert–butyl–5–oxooxazolidine–3–carboxylate for Convenient Preparation of D– and L–threonine Analogs from Aldehydes*', Liegigs Ann.

Shuji et al., *Nuclear Magnetic, Resonance Study of the Stereoisomeric 2–oxazolidinone and 2–phenyl–2–oxazoline Derivatives of .alpha.–amino–.beta.–hydroxy Acids*, Bulletin of the Chemical Society of Japan, vol. 46, No. 10, pp. 3308–3310 (1973).

*Primary Examiner*—James H. Reamer
*Attorney, Agent, or Firm*—Pillsbury Madison & Sutro, LLP

[57] ABSTRACT

The invention relates to a process for preparing α-amino acid amides, the corresponding α-amino acids, or salt thereof, which are substituted at the β-site with at least one (hetero)aromatic group. This is achieved according to the invention by subjecting a 4-carbamoyl-2-oxazolidinone compound, respectively a 4-carboxy-2-oxazolidinone compound, wherein each of them is substituted at the 5-site with at least one (hetero)aromatic group, to a treatment with $H_2$ in the presence of a catalyst. The invention also relates to a process for preparing a 4-carbamoyl-2-oxazolidinone compound substituted at the 5-site with at least one (hetero) aromatic group, in which process an α-amino-β-hydroxypropane nitrile substituted at the β-site with at least one (hetero)aromatic group, or a salt thereof, is subjected to a treatment in the presence of $CO_2$ and a base.

17 Claims, No Drawings

PROCESS FOR PREPARING α-AMINO ACID AMIDES, α-AMINO ACIDS AND DERIVATIVES THEREOF

FIELD OF THE INVENTION

The invention relates to a process for preparing α-amino acid amides, the corresponding α-amino acids, or salts thereof, which are substituted at the β-position with at least one (hetero) aromatic group.

α-Amino acid amides and the corresponding α-amino acids, with the β-position being substituted with at least one (hetero)aromatic group, are important, for instance, as raw materials for pharmaceutical and agrochemical products. Examples of such α-amino acids are tryptophan, tyrosine, histidine and phenylalanine.

The invention particularly relates to the preparation of phenylalanine, phenylalanine amide and salts thereof; and to the novel intermediate 4-carbamoyl-5-phenyl-2-oxazolidinone. Phenylalanine is an α-amino acid which is used, for instance, as an active component in the preparation of an artificial sweetener known as 'aspartame', which is the α-L-aspartyl-L-phenyl-alanine methyl ester.

BACKGROUND INFORMATION

From literature a number of routes are known for the synthesis of α-amino acid amides and the corresponding α-amino acids, in which the β-position is substituted with at least one (hetero)aromatic group. The best known route, which can be-used for different α-amino acids, is the Strecker synthesis route (Introduction to Organic Chemistry, Streitwieser and Heathcock, Macmillan Publishing Co., Inc. New York, 1981). In that method a suitable aldehyde is treated with ammonia and HCN, so that an α-amino nitrile is formed, which is subsequently subjected to a hydrolysis reaction.

The aldehyde used in the preparation of phenylalanine is phenylacetaldehyde. This raw material, however, is expensive. The Strecker synthesis is therefore economically unattractive for the production of phenylalanine on an industrial scale. That is why in the past efforts were made to find alternative and economically more profitable processes for the production of phenylalanine on an industrial scale. One of these processes is based on the intermediate hydantoin. This intermediate is condensed with benzaldehyde to form benzylidene hydantoin. After hydrogenation of the double bond and hydrolysis of the hydantoin ring phenylalanine is obtained.

Although the hydantoin process is often more advantageous economically than the Strecker process, hydantoin, too, is a relatively expensive raw material and consequently less attractive economically for the preparation of phenylalanine.

SUMMARY AND OBJECTS OF THE INVENTION

The object of the invention is to provide an alternative process for the preparation of α-amino acid amides, the corresponding α-amino acids, or salts thereof, which are substituted at the β-position with at least one (hetero) aromatic group.

This object is achieved according to the invention by subjecting the corresponding 4-carbamoyl- or 4-carboxy-2-oxazolidinone compound, which is substituted at the 5-position with at least one (hetero)aromatic group, to a treatment with $H_2$ in the presence of a catalyst.

Depending on the starting compound selected, viz. a 4-carbamoyl- or a 4-carboxy-2-oxazolidinone compound, to treatment causes the corresponding α-amino acid amide or, respectively, the corresponding α-amino acid to be formed, both of them substituted at the β-position with at least one (hetero)aromatic group. If the chosen starting material is a 4-carbamoyl-2-oxazolidinone compound, the α-amino acid amide obtained can subsequently, if desired, be hydrolyzed to form the α-amino acid according to processes that are well known in the art.

The process according to the invention is a technically simple and economically attractive alternative to the existing processes. With the process according to the invention high conversions (more than 90%) and high yields (more than 80%) can be realized, which makes the process economically highly attractive. Moreover, the process according to the invention provides an—environmentally advantageous—low-salt process, in contrast with the Strecker synthesis and the hydantoin process, which produce relatively more salt. Furthermore, the starting materials used, the 4-carbamoyl- or the 4-carboxy-2-oxazolidinone compound, can be made from cheap basic raw materials in a technically simple manner.

DETAILED DESCRIPTION OF THE INVENTION

The various α-amino acid amides, α-amino acids, or salts thereof, which can be prepared using the process according to the invention, may, for instance, be compounds of Formula 1,

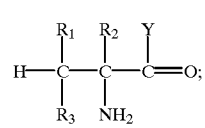

and salts thereof, where Y stands for an $NH_2$ or an OH group; $R_1$ and $R_2$ can be selected freely, independently of each other. Suitable choices for $R_1$ and $R_2$ are, for instance, hydrogen and (hetero)aromatic and aliphatic groups, particularly optionally substituted aryl, heteroaryl, alkyl, cycloalkyl or alkenyl groups. The (hetero)aromatic and aliphatic groups in $R_1$ and $R_2$ preferably have 1 to 20, more specifically 1 to 10 carbon atoms. Suitable substituents are those which are inert under the given reaction conditions, for instance alkyl or (hetero)aryl substituents. $R_3$ represents an optionally substituted (hetero)aromatic group. Examples of such a (hetero)aromatic group are an indolyl group, a p-hydroxyphenyl group, an imidazolyl group and a phenyl group.

2-Oxazolidinone compounds that can be used as starting materials can be represented by, for instance, Formula 2, where Y, $R_1$, $R_2$ and $R_3$ are defined by the choice of the α-amino acid acid or α-amino acid amide to be prepared, as defined above.

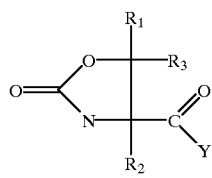

(2)

For the preparation of phenylalanine or the corresponding amide with the process according to the invention, the chosen starting material is 4-carbamoyl-5-phenyl-2-oxazolidinone or 4-carboxy-5-phenyl-2-oxazolidinone being a 2-oxazolidinone compound according to Formula 2, where substituents $R_1$ and $R_2$ are hydrogen and $R_3$ is a phenyl group and Y is an OH group or an $NH_2$ group.

A suitable embodiment of the process for the preparation of α-amino acid amides, the corresponding α-amino acids, or salts thereof, is, for instance, as follows: a 2-oxazolidinone compound, a catalyst and, if so desired, an inert solvent are combined in an autoclave to obtain a reaction mixture. The reaction mixture is subjected to the required temperature and pressure using $H_2$ (adding $H_2$).

The catalyst is used in an amount effective for the hydrogenolysis reaction (hydrogenation and hydrolysis) in which a 2-oxazolidinone is converted into the corresponding amino acid or amino acid amide (and $CO_2$). The catalyst used may, for instance, be a catalyst, optionally on a carrier, containing an element from Groups 7, 8, 9, 10 or 11 of the Periodic System (Handbook of Chemistry and Physics, 70th Edition, CRC Press, 1989–1990), for instance Re, Ru, Os, Rh, Pt, Pd, Ni or Ag. The carrier material selected may, for instance, be alumina, titanium dioxide, carbon, zirconium dioxide or silica. A very suitable catalyst is a palladium-on-carbon catalyst, for instance a catalyst having a palladium content of between 0.1 and 10 wt. % calculated on the total palladium and carbon content. The amount of catalyst to be used may vary within wide limits. The amount of catalyst can easily be determined by one skilled in the art. Good results were achieved with a Pd/C catalyst with a palladium content of 5 wt. % calculated on the total amount of palladium and carbon, used in amounts of 2 to 20 wt. % calculated on the starting material, the 2-oxazolidinone compound.

In principle, the solvent can be any solvent inert to the starting material and to the reaction product during the treatment. This solvent may be selected, for instance, from the group consisting of water, alcohols, hydrocarbons and ethers. Examples of suitable solvents are water, lower alcohols, for instance with 1–6 C atoms, particularly methanol, ethanol or mixtures of such solvents, for instance a mixture of water and a lower alcohol. Particularly good results were obtained with a mixture of water and methanol.

The treatment of the 2-oxazolidinone compound with $H_2$ and a catalyst is preferably carried out in an autoclave. The temperature is not particularly critical and is preferably selected between 0–150° C., and more particularly between 50–100° C.; in order to obtain optimum selectivity the selected temperature is preferably lower than 100° C. The pressure at which the treatment is carried out is not critical and is preferably between 0.2–2 MPa, and more particularly between 0.5–1 MPa.

The invention also relates to a process for preparing a 4-carbamoyl-2-oxazolidinone compound substituted at the 5-position with at least one (hetero)aromatic group, in which process an α-amino-β-hydroxy-propane nitrile substituted at the β-position with at least one (hetero)aromatic group, or a salt thereof, is subjected to a treatment in the presence of $CO_2$ and a base.

The advantage of such a process is that it is technically easy to be carried out, that it is economically quite attractive because the raw materials are readily commercially available, and that a high yield (more than 80%) can be realized. For instance, the α-amino-β-hydroxy-β-phenyl-propane nitrile, which can be used according to the invention for the preparation of phenylalanine, can very easily be prepared from, among other materials, such commercially available raw materials as formaldehyde, hydrocyanic acid, ammonia and benzaldehyde, or aminoacetonitrile and benzaldehyde.

α-Amino-β-hydroxy-propane nitriles substituted at the β-position with at least one (hetero)aromatic group may, for instance, be compounds having the general Formula 3

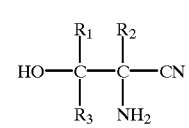

(3)

where substituents $R_1$, $R_2$ and $R_3$ have the same meanings as described above.

A suitable embodiment of the process for preparing the 4-carbamoyl-2-oxazolidinone compound substituted at the 5-position with at least one (hetero)aromatic group is as follows: an α-amino-β-hydroxy-propane nitrile or a salt thereof, according to Formula 3, a base and, if so desired, an inert solvent are combined. Then $CO_2$ is added to the reaction mixture. After the reaction, the end product can be recovered, for instance by allowing the end product to crystallize out and filter it off from the reaction mixture. In practice the resulting product is usually pure enough for the preparation of β-substituted α-amino acid amides, the corresponding α-amino acids, or salts therof.

The product thus obtained, the 4-carbamoyl-2-oxazolidinone compound, can if desired also be hydrolyzed according to processes known in the art to obtain the corresponding 4-carboxy-2-oxazolidinone compound.

$CO_2$ can be added in the form of a gas or as supercritical $CO_2$, but it is also possible for the $CO_2$ to be formed in situ in the reaction mixture from a $CO_2$ precursor. The amount of $CO_2$ is not critical. The amount of $CO_2$ used is preferably 0.8–10 eq. relative to the nitrile. If complete conversion is aimed at, the amount of $CO_2$ added to the reaction mixture is at least 1 eq. relative to the nitrile.

The base that is used may, for instance, be an organic or an inorganic base. Examples of such bases are aliphatic or aromatic amines, ethanol amines, guanidine, alkali carbonates and alkali hydrogen carbonates. Very good results were obtained with triethyl amine, ammonia and sodium hydrogen carbonate.

The base is preferably used in an amount of 0.1–10 eq. relative to the α-amino-β-hydroxy-propane nitrile. If the salt of the amino nitrile is used, at least an equivalent amount of the base is needed in order also to fully liberate the salt. In this case use an amount of base ranging from 1.1 to 11 eq. relative to the α-amino-β-hydroxy propane nitrile to be liberated is preferably used.

The temperature during the treatment with $CO_2$ and a base is not critical. The treatment is preferably carried out at a temperature between 0 and 100° C., particularly between 20 and 80° C.

The solvent used may in principle be any solvent that is inert to the starting material, the other reactants and the reaction product during the treatment. Suitable solvents are, for instance, the solvents described above for the treatment of a 2-oxazolidinone compound in the presence of $H_2$ and a catalyst.

The process for preparing a 4-carbamoyl-2-oxazolidinone compound substituted at the 5-position with at least one (hetero)aromatic group can be followed by a process for the treatment of this compound in the presence of $H_2$ and a catalyst so that the corresponding α-amino acid amide is formed. This α-amino acid amide can be hydrolyzed, if so desired, to form the α-amino acid according to processes known in the art.

The process for preparing a 4-carbamoyl-2-oxazolidinone compound substituted at the 5-position with at least one (hetero)aromatic group can be followed also by a hydrolysis of the 4-carbamoyl-2-oxazolidinone compound, so that the 4-carboxy-2-oxazolidinone compound is formed, which can then be treated in the presence of $H_2$ and a catalyst to form the corresponding α-amino acid.

The two processes mentioned above constitute a simple and economically attractive route for the preparation of α-amino acid amides, the corresponding α-amino acids, or salts thereof, which are substituted at the β-position with at least one (hetero)aromatic group. The invention therefore also relates to this particularly attractive alternative process for the preparation of α-amino acids, α-amino acid amides or salts thereof from readily accessible raw materials. An added advantage of this process for preparing α-amino acids, α-amino acid amides or salts thereof is that the two steps described above, viz. the preparation of a 4-carbamoyl-2-oxazolidinone compound using $CO_2$ and a base and the treatment of this compound in the presence of $H_2$ and a catalyst, can be carried out in the same solvent and in the same reactor vessel, which makes the implementation technically simple, for instance due to the fact that fewer separation and purification steps have to be carried out. Another advantage of the process is that a high yield (more than 80%) can be realized.

The process according to the invention will now be further elucidated by means of the following examples without, however, being limited thereto.

EXAMPLE I

Preparation of α-amino-β-hydroxy-β-phenylpropane Nitrile

Ia) Preparation of N-benzylidene-aminoacetonitrile

The preparation was carried out in a nitrogen atmosphere. 50 g (0.54 mole) of the HCl salt of amino acetonitrile was dissolved in 130 ml $H_2O$. Using an aqueous NaOH solution (50 wt. %) the pH was brought to 7. With vigorous stirring 54.60 ml (0.54 mole) benzaldehyde was added in one single step. Immediately a white deposit was formed. The pH fell to 6. The pH was raised to 7 again using a portion of abovementioned aqueous NaOH solution. The reaction mixture was stirred at room temperature for 3 hours. Subsequently, 100 ml diethyl ether was added and the two layers were separated. The water layer was washed twice using 100 ml diethyl ether. The organic layers collected were dried using $MgSO_4$, filtered off and evaporated. The product was a pale yellow oil. The oil was distilled in a vacuum (vacuum pump). At 112° C. a colourless fraction came off at the top. Yield: 62.51 g (0.42 mole, 78%) $^1H$ NMR (200 MHz, $CDCl_3$) δ (ppm): 4.55 (2H, s, $CH_2$), 7.42 (3H, m, Ph), 7.75 (2H, m, Ph), 8.42 (1H, m, CH); $^{13}C$ NMR (200 MHz, $CDCl_3$) δ (ppm): 45.66 ($CH_2$), 115.68 (CN), 128.65 (Ph), 128.85 (Ph), 131.86 (Ph), 134.84 (Ph), 164.78 (CH).

Ib. Preparation of α-(N-benzylidene)-amino-β-hydroxy-βphenylpropane Nitrile The preparation was carried out in a nitrogen atmosphere. To a solution of 5.16 g (35.83 mmoles) N-benzylidene amino acetonitrile in a mixture of 4.20 ml toluene and 5.15 ml $H_2O$ 0.35 g of an aqueous NaOH solution (2.25 mmoles, 25 wt. %) was added at room temperature and 3.60 ml (35.83 mmoles) benzaldehyde was slowly added dropwise. The reaction mixture was intensively stirred for 3 hours. A thick yellow slurry was formed. The water layer was removed using a pipette and the organic phase was evaporated. The product was obtained in the form of a yellow solid (9.23 g); purity in terms of α-(N-benzylidene)-amino-β-hydroxy-β-phenylpropane nitrile: 88% (29 mmoles); yield: 81%; melting point 83–84° C.; $^1H$ NMR (200 MHz, $CDCl_3$) δ (ppm): 4.86 (1H, dd, J=4.24, 1.59 Hz, NCHCN), 5.20 (1H, d, J=4.24 Hz, HOCHPh), 7.25–7.10 (3H, m, Ph), 7.58–7.32 (10H, m, Ph), 7.78 (2H, m, Ph), 8.50 (1H, s, Ph, CH=N); $^{13}C$ NMR (200 MHz, $CDCl_3$) δ (ppm): 66.11 (NCHCN), 74.09 (HOCHPh), 115.29 (CN), 126.83 (Ph), 129.69 (Ph), 132.06 (Ph), 134.49 (Ph), 138.19 (Ph), 165.19 (PhCH=N).

Ic) Preparation of α-amino-β-hydroxy-β-Phenylpropane Nitrile

A slurry of 2.5 g crude α-(N-benzylidene)-amino-β-hydroxy-β-phenylpropane nitrile (pure: 1.26 g, 0.005 mole), 2 ml toluene and 5 ml 1N aq. $H_2SO_4$ solution (0.005 equivalent $H^+$) was firmly stirred at 50–60° C. for 2 hours. The pH of the reaction mixture was measured and found to be 0. After the reaction, a pale yellow deposit had formed. The reaction mixture was evaporated and 15 ml MeOH was added. The deposit was filtered off and washed once using MeOH. The white solid was dried overnight in a vacuum at 45° C. The yield was 0.92 g (71%) of the bisulphate salt.

EXAMPLES II TO V

Preparation of 4-carbamoyl-5-phenyl-2-oxazolidinone

To a solution of α-amino-β-hydroxy-β-phenylpropane nitrile bisulphate salt (6 g, 23 mmoles) in 50 ml $MeOH/H_2O$ (m:m/1:1) triethylamine (TEAM) (9.6 g, 69.2 mmoles) was added. Subsequently, for 6 hours $CO_2$ was bubbled through the solution at 40° C. During the reaction the pH of the solution fell from 9.7 to 7.8. A white solid substance crystallized out of the solution. This substance was filtered off and dried in a vacuum. The yield was 4.7 g (22.8 moles, 99 wt. % ), obtained in the form of white crystals having a melting point: 249–250° C.; $^1H$ NMR (200 MHz, DMSO) d (ppm): 3.30 (0.5H, s, $H_2O$), 4.42 (1H, δ, J=8.37 Hz, NCHCO), 5.79 (1H, d, J=8.37 Hz, OCHPh), 6.85 (1H, s, NH), 7.20 (1H, s, NH), 7.30 (5H, m, Ph), 8.00 (1H, s, NH); $^{13}C$ NMR (200 MHz, DMSO) δ (ppm): 59.41 (NCHCO), 78.75 (OCHHPh), 126.82 (Ph), 127.94 (Ph), 128.41 (Ph), 135.44 (Ph), 15.02 (NC=OO), 169.77 (C=$ONH_2$); IR (KBr,$cm^{-1}$): 3396 ($NH_2$), 3273 ($NH_2$), 3200, 1740 (C=O), 1719, 1684 (C=O), 1611 Mass (EI): 206 M, 189, 163, 105, 77, 44. The experiment was repeated under different conditions. The results are shown in Table 1.

TABLE 1

| Ex. | salt (mmoles) | Temp. (° C.) | Solvent (m:m) | Base (eq.) | Yield (%) |
|---|---|---|---|---|---|
| II | 23.00 | 40 | MeOH/H$_2$O (1:1) | 3 TEAM | 99 |
| III | 7.69 | 40 | EtOH/H$_2$O (1:1) | 3 TEAM | 89 |
| IV | 3.85 | 75 | H$_2$O | 3 NaHCO$_3$ | 66 |
| V | 3.85 | 60 | H$_2$O | 3 NH$_3$ | 58 |

EXAMPLES VI TO VIII

Preparation of Phenylalanine Amide

In a 50-ml Hastelloy C-276 autoclave 4-carbamoyl-5-phenyl-2-oxazolidinone (1 g, 4.9 mmoles), 25 ml MeOH/H$_2$O (m:m=1:1) and Pd/C catalyst (0.21 g, 10 wt. %, of a 5% Pd content on carbon catalyst) were mixed. The autoclave was purged 3 times using N$_2$ and after that 3 times using H$_2$. The temperature was brought to 50° C. and the autoclave was stirred for 30 minutes under an H$_2$ pressure of 8 bar. Afterwards the reactor mass was analyzed using HPLC. The conversion was 100% and the selectivity to phenylalanine amide 89%. The experiment was repeated under different conditions. The results are shown in Table 2.

TABLE 2

| Ex. | time (h) | solvent (m:m) | catalyst wt. % | conversion (%) | select. NH$_2$ (%) | yield (%) |
|---|---|---|---|---|---|---|
| VI | 0.5 | MeOH/H$_2$O (1:1) | 10 wt. % Pd/C | 100 | 89 | 89 |
| VII | 0.5 | MeOH/H$_2$O (1:1) | 1 wt. % Pd/C | 100 | 91.5 | 91.5 |
| VIII | 1 | H$_2$O | 10 wt. % Pd/C | 100 | 84 | 84 |

What we claim is:

1. A process for preparing an α-amino acid amide substituted at the β-position with at least one optionally substituted aryl group, or a salt thereof, comprising:

subjecting a 4-carbamoyl-2-oxazolidinone compound represented by the formula:

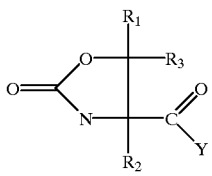

wherein

Y represents —NH$_2$ or —OH,

R$_1$ represents hydrogen or an alkyl group,

R$_2$ represents hydrogen, and

R$_3$ represents an aryl group to a treatement with H$_2$ in the presence of a catalyst under effective hydrogenolysis conditions to cleave the carbon oxygen bond in the oxazoline ring, whereby an α-amino acid amide or salt thereof is obtained.

2. A process according to claim 1, wherein Y represents —NH$_2$.

3. A process according to claim 1, wherein the aryl group contains 6 to 20 carbon atoms.

4. A process according to claim 2, wherein the process comprises the further step of subjecting the α-amino acid amide or a salt thereof to a hydrolysis reaction.

5. A process according to claim 1, wherein R$_3$ represents a p-hydroxyphenyl group or a phenyl group.

6. A process according to claim 1, wherein R$_1$ is hydrogen or methyl.

7. A process according to claim 1, wherein R$_1$ is hydrogen.

8. A process according to claim 5 or 7, wherein R$_3$ is phenyl.

9. A process according to claim 1, wherein said process further comprises subjecting an α-amino-β-hydroxypropane-nitrile substituted at the β-position with said aryl group, or a salt thereof, to a treatment in the presence of CO$_2$ and a base whereby a 4-carbamoyl-2-oxazolidinone compound substituted at the 5-position with said aryl group is obtained.

10. A process according to claim 9, wherein the substituent at the β-position is phenyl.

11. A process according to claim 9 or 10, wherein said base is selected from the group consisting of ammonia, aromatic amine, aliphatic amine, ethanol amine, guanidine, alkali hydrogen carbonates and alkali carbonates.

12. A process for preparing a 4-carbamoyl-2-oxazolidinone compound substituted at the 5-position with an aryl group comprising subjecting an α-amino-β-hydroxy-propane nitrile substituted at the β-position with said aryl group, or a salt thereof, to a treatment in the presence of CO$_2$ and a base.

13. A process according to claim 12, wherein said α-amino-β-hydroxy-propane nitrile substituted at the β-position with said aryl group, or a salt thereof, is represented by the formula:

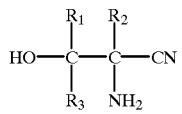

wherein

R$_1$ represents hydrogen or alkyl,

R$_2$ represents hydrogen, and

R$_3$ represents an aryl group.

14. A process according to claim 12 or 8, wherein said base is selected from the group consisting of ammonia, aromatic amine, aliphatic amine, ethanol amine, guanidine, alkali hydrogen carbonates and alkali carbonates.

15. A process according to claim 12, wherein said process further comprises hydrolyzing the resulting 4-carbamoyl-2-oxazolidinone compound substituted at the 5-position with said aryl group.

16. A process according to claim 15, wherein the aryl group is a phenyl group or p-hydroxyphenyl.

17. 4-Carbamoyl-5-phenyl-2-oxazolidinone.

* * * * *